(12) United States Patent
Mullenger et al.

(10) Patent No.: US 8,484,049 B2
(45) Date of Patent: Jul. 9, 2013

(54) TISSUE TRACKING

(75) Inventors: Robert L. Mullenger, Mountain View, CA (US); James Rickaway, Lebanon, TN (US); Kevin Carnes, Gallatin, TN (US); Suzanne Alexander-Vaughn, Lebanon, TN (US); James Cline, Norcross, GA (US)

(73) Assignee: Omnicell, Inc., Mountain View, CA (US)

( * ) Notice: Subject to any disclaimer, the term of this patent is extended or adjusted under 35 U.S.C. 154(b) by 395 days.

(21) Appl. No.: 12/500,481

(22) Filed: Jul. 9, 2009

(65) Prior Publication Data

US 2010/0198620 A1  Aug. 5, 2010

Related U.S. Application Data

(60) Provisional application No. 61/148,774, filed on Jan. 30, 2009.

(51) Int. Cl.
*G06F 19/00* (2011.01)

(52) U.S. Cl.
USPC ............................................................ 705/3

(58) Field of Classification Search
USPC . 705/1, 2, 3; 340/5.73; 235/385, 382; 62/440
See application file for complete search history.

(56) References Cited

U.S. PATENT DOCUMENTS

| | | | |
|---|---|---|---|
| 4,415,802 A * | 11/1983 | Long | 235/382 |
| 5,190,185 A | 3/1993 | Blechl | |
| 5,377,864 A | 1/1995 | Blechl et al. | |
| 5,745,366 A | 4/1998 | Higham et al. | |
| 5,805,455 A | 9/1998 | Lipps | |
| 5,805,456 A | 9/1998 | Higham et al. | |
| 5,842,179 A | 11/1998 | Beavers et al. | |
| 5,905,653 A | 5/1999 | Higham et al. | |
| 5,927,540 A | 7/1999 | Godlewski | |
| 6,011,999 A | 1/2000 | Holmes | |
| 6,039,467 A | 3/2000 | Holmes | |
| 6,151,536 A | 11/2000 | Arnold et al. | |
| 6,170,929 B1 | 1/2001 | Wilson et al. | |
| 6,272,394 B1 | 8/2001 | Lipps | |
| 6,385,505 B1 | 5/2002 | Lipps | |
| 6,604,019 B2 | 8/2003 | Ahlin et al. | |
| 6,609,047 B1 | 8/2003 | Lipps | |
| 6,640,159 B2 | 10/2003 | Holmes et al. | |
| 6,675,166 B2 | 1/2004 | Bova | |
| 6,760,643 B2 | 7/2004 | Lipps | |
| 6,975,922 B2 | 12/2005 | Duncan et al. | |
| 7,072,855 B1 | 7/2006 | Godlewski et al. | |
| 7,218,231 B2 | 5/2007 | Higham | |
| 7,348,884 B2 | 3/2008 | Higham | |

(Continued)

OTHER PUBLICATIONS

PCT International Search Report and Written Opinion mailed Mar. 30, 2010; International Application No. PCT/US2010/022512, 8 pages.

*Primary Examiner* — John Pauls
(74) *Attorney, Agent, or Firm* — Kilpatrick Townsend & Stockton LLP

(57) ABSTRACT

A tissue tracking system is disclosed that provides tissue tracking, for example, at medical facilities. The tissue tracking system may be incorporated with a supply chain, billing, inventory, and/or order systems. In some embodiments, the tissue tracking system may also track environmental conditions of the tissue during reception, storage and issuance. Tissue sequestration methods are also disclosed.

20 Claims, 13 Drawing Sheets

U.S. PATENT DOCUMENTS

| | | | |
|---|---|---|---|
| 2002/0178016 A1* | 11/2002 | McLellan | 705/1 |
| 2003/0154105 A1 | 8/2003 | Ferguson | |
| 2005/0262088 A1 | 11/2005 | Solis et al. | |
| 2005/0264400 A1* | 12/2005 | Fisher | 340/5.73 |
| 2006/0054694 A1* | 3/2006 | Auchinleck | 235/385 |
| 2008/0077433 A1 | 3/2008 | Kasprisin et al. | |
| 2008/0098329 A1 | 4/2008 | Csore et al. | |
| 2008/0104993 A1* | 5/2008 | Zenobi et al. | 62/440 |

\* cited by examiner

Tissue Issue Entry

434F01S87302
*Skin Graft*
Allograft

Scan or Key Serial #: S0089483903GGED56

| User ID | Name | Date / Time |
|---|---|---|
| Preparer: 123456 | Abel, Nurse ▼ | MM/DD/YY ▲▼ 10:59 AM |
| Accepter: 234567 | Brown, Nurse ▼ | MM/DD/YY ▲▼ 11:13 AM |
| Issuer: 345678 | Charlie, Nurse ▼ | MM/DD/YY ▲▼ 11:15 AM |

☐ Package Integrity is Acceptable
☐ Tissue Temperature Within Acceptable Range

[Cancel]  [OK]

*FIG. 5*

TISSUE TRACKING

CROSS REFERENCE TO RELATED APPLICATIONS

This application claims the benefit of commonly assigned U.S. Provisional Patent Application No. 61/148,774, filed Jan. 30, 2009, entitled "Bone and Tissue Tracking," the disclosure of which is herein incorporated by reference for all purposes.

BACKGROUND

Recent regulations have tightened tissue handling in clinical laboratories, surgery centers, outpatient centers and tissue banks Tissue handling occurs in nearly 1600 hospitals in the United States. These hospitals, on average, provide over 100 beds of surgical services with at least five operating suites handling. Because of large patient populations and the multifarious tissues handled within such facilities, compliance with tissue handling requirements can be daunting.

BRIEF SUMMARY

A tissue tracking system is disclosed that tracks tissue according to regulatory requirements. Such tissue tracking systems may be integrated with existing supply chain, billing, inventory, patient statistic, and/or ordering systems. In some embodiments, the tissue tracking system may be integrated with cabinets such as, for example, storage cabinets, supply rooms, refrigerators, etc. In some embodiments, tissue may only be stored and/or issued from approved cabinets. In some embodiments, tissue tracking systems may restrict and/or limit how the tissue is physically tracked. In some embodiments, tissue tracking system may maintain digital records of the tissue as it moves from reception to issuance. Such information may include environmental data, handler ids, source information including validation, dates and times, serial numbers, locations, etc.

Tissue serialization systems and methods are also disclosed. In some embodiments, tissue serialization may generate and/or provide serial numbers for received tissues. In some embodiments, a unique serial number is provided for each tissue received. In other embodiments, source serial numbers may be used for serialization. In some embodiments, serialization may incorporate previously existing bar codes or the creation of new bar codes to aid in tracking. In some embodiments, serialization may also include inputting source information, tissue shipment compliance, environment factors during shipping, licensure of source agency, uploading of credential, etc. In some embodiments, serialization may also include source validation processes.

Tissue tracking methods and systems that track the temperature of tissue are also disclosed. For example, the temperature of tissue may be recorded and saved in association with tissue information at predetermined intervals. In some embodiments, if the temperature of the tissue or cabinet varies from previously determined minimums and/or maximums, an alert may be initiated and/or a note may be made in a file association with tissue information. Tissue storage devices are also disclosed that communicate temperature data with a tissue tracking system. Cabinet locks and temperature reading and communication device may also be used with existing systems to incorporate them with a temperature tracking system.

Tissue sequestration methods and systems are also provided. Tissue may be sequestered, for example, based on information from the source regarding infection or disease. In some embodiments, sequestered tissue, for example, may not be issued while sequestered. In some embodiments, new tissue may be automatically ordered as needed while tissue is sequestered. Tissue may be un-sequestered and once again be available for issuance.

Adverse event tracking systems and methods are also provided. When an adverse event in the chain of the tissue from the source through to issuance is noted, the tissue tracking system may know who to notify and how best to notify them based on the tracking information and patient records associated therewith.

BRIEF DESCRIPTION OF THE DRAWINGS

FIG. 5 shows a screenshot of form for entering data prior to issuing tissue from a storage cabinet according to some embodiments.

DETAILED DESCRIPTION

Various embodiments of the invention provide for a tissue tracking system that tracks tissue from reception to issuance. In some embodiments, a tissue tracking system maintains tissue records that satisfy regulatory requirements. Such records can be updated based on the tissue location, environment, issuance, source information, etc. Moreover, the records can be associated with a patient, a tissue supplier, tissue handlers, etc. Moreover, tissue tracking systems can coordinate with supply chain management systems, billing systems, patient record systems, etc.

The term "tissue" as used throughout this disclosure includes any type of tissue specimens including bone, cornea, skin, heart tissue, valves/conduits, tendons, ligaments, fascia, dura, bone marrow, veins, arteries, cartilage, organ, sperm, embryo, muscles, egg, cells, stem cells, cord blood, synthetic tissue (artificially prepared, human and nonhuman based), and other cellular—and tissue-based transplant or implant products. Moreover, tissue can refer to allograft tissue, autograft tissue, isograft tissue, and/or xenograft tissue.

Tissue tracking systems as described throughout this disclosure can be used to document tissue from reception at a facility to issuance to a patient. Regulation and best practices can require or recommend to handle tissue different than other medical supplies. Documentation can be used to track tissue from reception at a facility, to storage, and through to issuance to a patient. Such documentation can be used to ensure compliance with regulation. Such documentation can be used to link tissue source information with patient information. Such information can be used to replenish tissue supplies and/or for billing purposes. Tissue documentation can be used ensure tissue is properly handled and stored. Moreover, tissue tracking systems can be used to sequester tissue that are discovered to be from a defective source or stored in an adverse environment.

Figure 1:
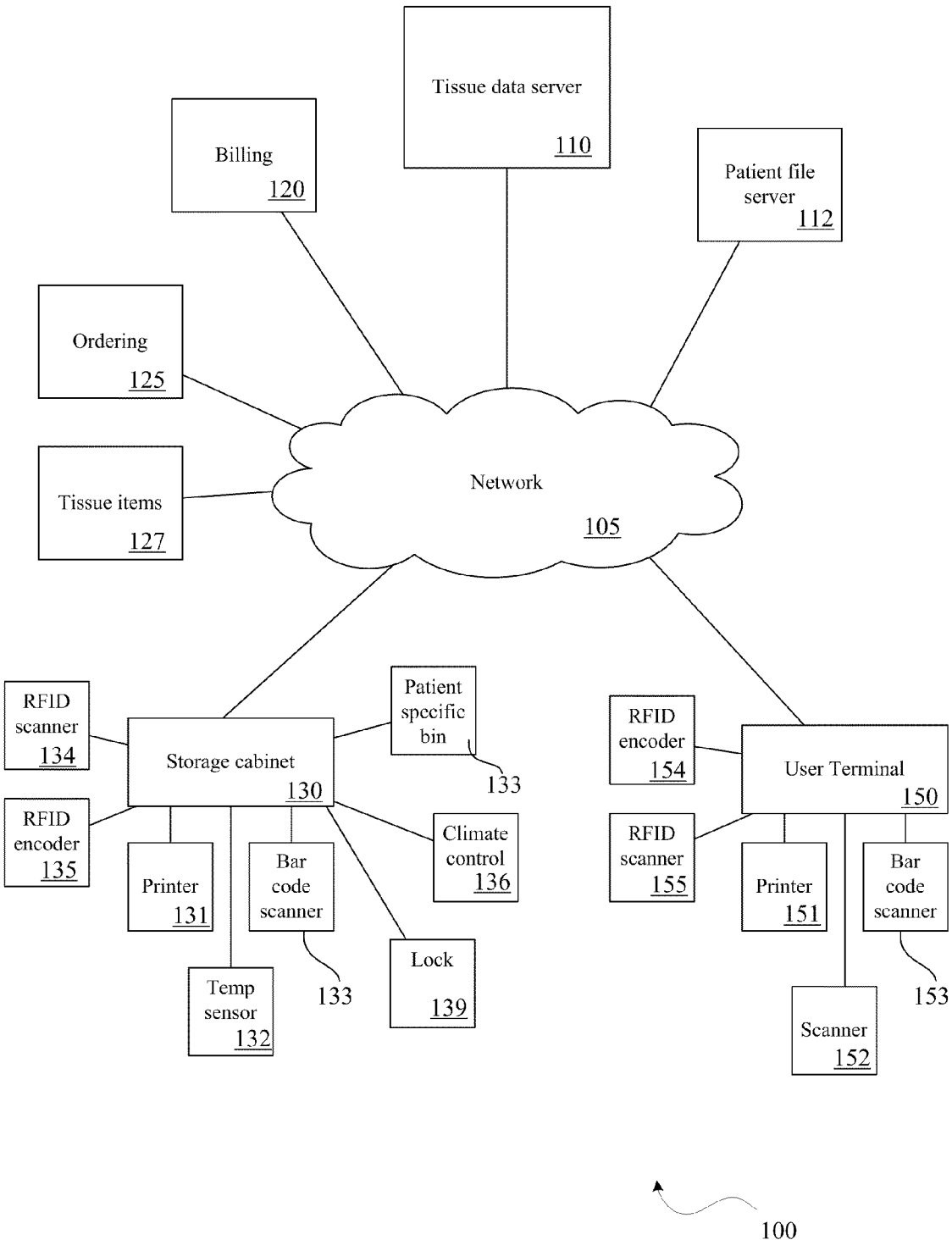
FIG. 1 is a block diagram of a tissue tracking system according to one embodiment.

FIG. 1 shows a block diagram of tissue tracking system 100 according to one embodiment of the invention. Tissue tracking system 100, for example, can be implemented in a hospital, medical office, or laboratory. Tissue tracking system 100 can include various subsystems communicatively interconnected through network 105. In some embodiments, tissue tracking system 100 includes tissue data server 110. Tissue data server, for example, can be a computer, file server, database server, etc. Tissue data server 110, in some embodiments, can store tissue data, such as, serial numbers, environmental data, usage data, time data, files, images, folders, documents, etc. related to a tissue being tracked by tissue tracking system 100. Tissue data server 110, in some embodiments, can associate various tissue data with a serial number within tissue data server 110. Tissue data server 110 can store data in any of various data structures that can link data of various types and from various sources that are associated with a tissue being tracked in the tissue tracking system 100. For example, tissue data can be stored using linked lists or lookup tables that link serial numbers with various other data. In some embodiments, tissue data server 110 includes a database of tissue records and/or data.

In some embodiments, tissue data server 110 can be part of a general supply management system and/or medical record system. The records maintained by the tissue data server 110 can also be similar to patient medical records and/or inventor systems. In some embodiments, a digital record can include a flag that indicates an item as tissue. In some embodiments, a separate flag can indicate if the tissue is autograft tissue.

In some embodiments, tissue data server 110 can be located in a remote location and can be accessed through a local area network or through the Internet. In some embodiments, tissue data server 110 can include multiple storage locations in one or more locations. In some embodiments, tissue data server 110 can include servers or can be coupled with servers that store data off-site and may include nightly backup of all data and/or can use encryption methods when transferring data.

In some embodiments, tissue tracking system 100 can include user terminal 150 coupled with the other subsystems through network 105. In some embodiments, more than one user terminal can be included. A user terminal, in some embodiments, can be a standard personal computer and can include various user input devices such as a mouse and/or keyboard as well as a display. Moreover, user terminal 150 can be coupled with or associated with other subsystems. User terminal 150 can include RFID scanner 155, RFID encoder 154, barcode scanner 153 and/or printer 151. User terminal 150 can be used, in some embodiments, to enter and or look up data stored within tissue data server 110.

In some embodiments, user terminal 150 can be used to receive tissue from a third party and enter the tissue into the tissue tracking system 100. In some embodiments, information related to incoming tissue may be recorded at user terminal 150. For example, such information can include a tissue serial number provided by the tissue provider, expiration date, the identification of the person accepting the tissue, source facility, department receiving the tissue, tissue expiration date, tissue type, patient medical record number (e.g., for autograft tissue), and the date and time of receipt. In some embodiments, the tissue serial number can be entered from an RFID tag affixed to the tissue packaging using RFID scanner 154 or a barcode affixed to the tissue packaging using bar code scanner 153. In some embodiments, comments related to the packaging and transport conditions of the tissue such as, for example, tissue integrity, packaging integrity, and temperature levels during transport, can be entered using user terminal 150. In some embodiments, billing information can be entered during reception such as billing entity, billing address, amount of bill, purchase order number, etc. Tissue source information can also be entered using user terminal 150. In some embodiments, tissue source information and or transport information can be scanned into the system using scanner 152.

In some embodiments, a tissue tracking system may validate the source of tissue as licensed by government agencies such as the U.S. Food and Drug Administration or the equivalent. Such information can be stored with tissue tracking information. In some embodiments, licensure may be tracked based on non-governmental organizations.

In some embodiments, a tissue tracking system may store, track, and/or provide information related to the source facility's storage, handling and use. In some embodiments, this information may be used to change environmental parameters in cabinets, refrigerators etc. In some embodiments, this information may be provided to a user when tissue is pulled for transport.

In some embodiments, tissue can be received without a serial number. A unique tissue serial number can be provided by the tissue data server and/or the user terminal and printed on a label using printer 151 along with a barcode representing the unique serial number. The label can then be affixed to the tissue packaging. In some embodiments, a barcode associated with a provided serial number can be printed on a label using printer 151. In some embodiments, an RFID system can be implemented and a unique RFID tag can be affixed to incoming tissue and used to track the tissue through the system.

Figure 4:
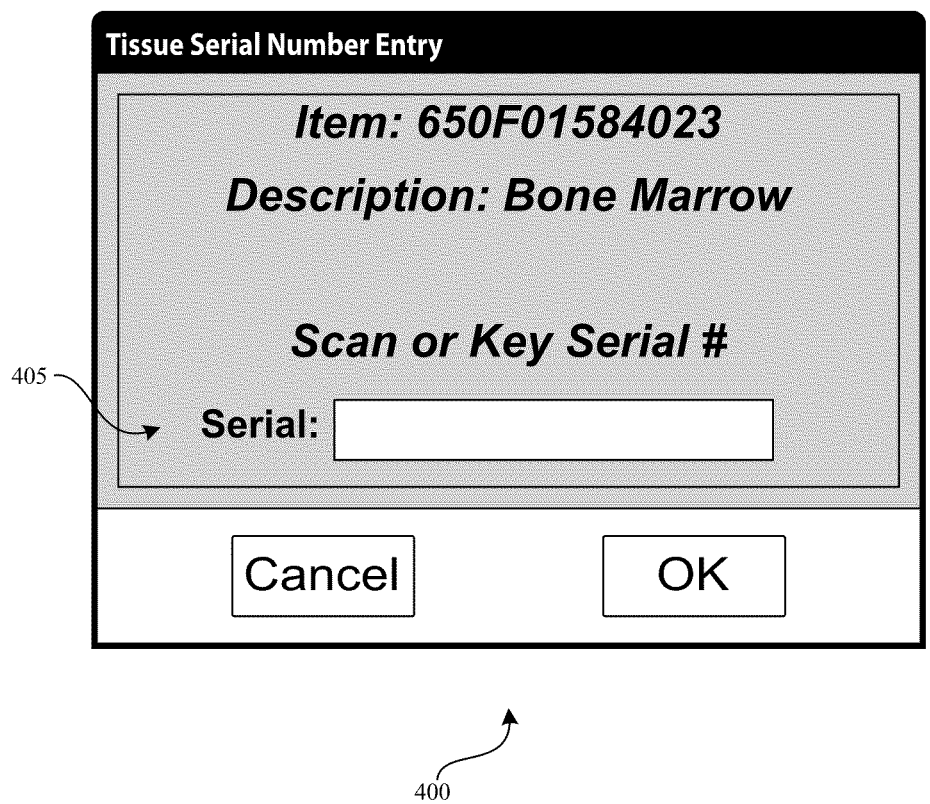
FIG. 4 is an example of a screenshot of an interactive display for issuing tissue.

FIG. 4 shows an example of a screen shot that can be used by a user at user terminal 150 to enter tissue data during reception. In some embodiments, if the tissue being received is autograft tissue, a serial number for the item may be generated automatically. For example, the format of the serial number may be, "TAyyyymmddsss", where yyyymmdd is the year, month, day and "sss" is the serial number. This number may be generated as soon as both the Autograft option is selected by a user at user terminal 150 and/or the patient from which the autograft came is selected. A label can be printed that includes the serial number (e.g. in readable characters and/or a barcode), the patient Medical Record Number, and/or the shelf label of the item. This label can be attached to the tissue packaging and can be scanned to identify the item when it is issued back to the patient.

In some embodiments, user terminal 150 can be located within an operating room. In such embodiments, a user can enter implantation records directly into the tissue data server 110 directly from within the operating room.

In some embodiments, a user terminal can include an administrator operations that allows access to add new users, reset passwords, and/or change access levels, as well as access, update, and/or revise tissue records stored in tissue data server 110. In some embodiments, four different levels of access to serve operating room management, staff, administration, etc. In some embodiments, a tissue tracking system may provide or produce a Tissue Implant Record that may, for example, be offered in an email to a supplier. In some embodiments, data fields/codes for each tissue may be bar code scanner compatible or RFID compatible. In some embodiments, the regulatory status of tissue suppliers may be maintained and/or displayed to a user; for example, including FDA approvals and/or AATB accreditations.

Tissue tracking system 100, in some embodiments, can include storage cabinet 130. In some embodiments, more than one storage cabinet 130 can be located in various locations within a facility. For example, storage cabinets can be located near operating rooms for quick access to tissue. Storage cabinet 130 can include a user interface that can be used to communicate information to a user and/or receive information from a user. For example, the user interface can include a display, a touch screen, a keyboard, a mouse, etc.

Storage cabinet 130 can be an open or closed cabinet. In some embodiments, storage cabinet 130 can be a shelf or a storage location. In some embodiments, storage cabinet can include a number of storage bins of different sizes and/or configurations for storing tissue and/or supplies of various sizes and shapes. Moreover, in some embodiments, storage cabinet 130 can include patient specific bins 133 that are provided to store tissue for a specific patient. Such bins, for example, can be organized by patient number, by room number, or in a first-in-first-out manner.

In some embodiments, storage cabinet 130 can include lock 139 that can be used to secure items within storage cabinet 130. Lock 139 can include a physical lock that is opened using a key, or an electronic lock that is opened using a card scanner, pass code, biometric, username, etc. Lock 139 can be used to secure items within storage cabinet 130 such that storage cabinet 130 can be accessed only by specific personal using a user id, biometric, id card, username, key, and/or pass code.

In some embodiments, storage cabinet 130 can include climate control devices 136. For example, climate control can include a refrigeration unit, heater, and/or humidifier. Climate control devices 136 can be used in conjunction with sensors, such as temperature sensor 132, to maintain the climate within storage cabinet 130.

In some embodiments, storage cabinet 130 can be coupled with a computer, processor and/or user terminal that can be configured to manage supply, environmental factors within in the cabinet and/or provide a user interface. In some embodiments, storage cabinet 130 can contain patient specific tissue bins.

In some embodiments, storage cabinet 130 can provide tissue availability information and tissue inventory information. In facilities with multiple tissue storage cabinets 130, each cabinet can include a unique cabinet identifier that distinguishes the storage cabinet from other cabinets. In some embodiments, when tissue is presented at a storage cabinet 130, a user can scan a bar code affixed to the tissue using bar code scanner 133 or RFID scanner 134 providing the tissue's serial number to the tissue tracking system. In some embodiments, prior to placing tissue within storage cabinet 130 the user may also present a user ID. In some embodiments, tissue serial number, the time, user ID, etc. can be communicated to tissue data server 110 for entry in association with the tissue serial number.

In some embodiments, storage cabinet 130 can also include a printer 131 and/or an RFID encoder 135. Printer 131 can be used, for example, to provide a label with a serial number, provide a label indicating tissue is sequestered, or any other label. RFID encoder can be used, for example, to encode an RFID tag associated with the tissue.

Some facilities such as large hospitals can include various supply chain cabinets for storing and dispensing various medical supplies. In some embodiments, tissue can be stored only within licensed storage facilities. If a user scans a bar code or an RFID tag associated with the tissue at a non-licensed station, based on the tissue records the tissue will be identified as tissue, and the user may receive a message like the message shown in FIG. 8, which indicates to the user that the station is unlicensed. The user, in some embodiments, must acknowledge the message with "OK".

In some embodiments, storage cabinet 130 can be attached to a hospital's refrigeration or freezer unit and/or can be include a stand alone refrigeration and/or freezer unit. Such storage cabinets 130 can provide secure storage for temperature-sensitive tissue. Storage cabinet 130 can include temperature sensor 132 that can record temperature data at predefined and/or set intervals. Such temperature data can be communicated to tissue storage server 110. The frequency of recording temperature data can be specified when the tissue is received by any user from any user terminal 150, at storage cabinet 130, and/or at the tissue data server 110. In some embodiments, the frequency can be set automatically based on the type of tissue, based on regulatory requirements, based on source requirements, by default (e.g., 30 minutes), etc. A user can specify the frequency of temperature tracking for each tissue or for groups of tissues.

In some embodiments, temperature minimums and maximums can be inputted and/or entered from source requirements. In some embodiments, when the temperature falls outside the minimums and/or maximums an audible and/or visual alarm may sound, a temperature reading may be logged, and/or an email, page, voicemail, text message, etc. can be sent to a previously indicated person.

In some embodiments, when the temperature is found to be out of range within storage cabinet 130, a "Temperature Out of Range" report can be created that indicates the cabinet, date, time, cabinet temperature, the tissue located within the cabinet. A system administrator can use such data to document temperature alarm resolution. In some embodiments, such a report may provide resolution and signature lines on the report. A system administrator can use this report to manually transcribe the resolution of the alarm, date and time of resolution and by whom. This report may generate at configurable time intervals until the temperature state returns to normal (user defined range).

Figure 10:
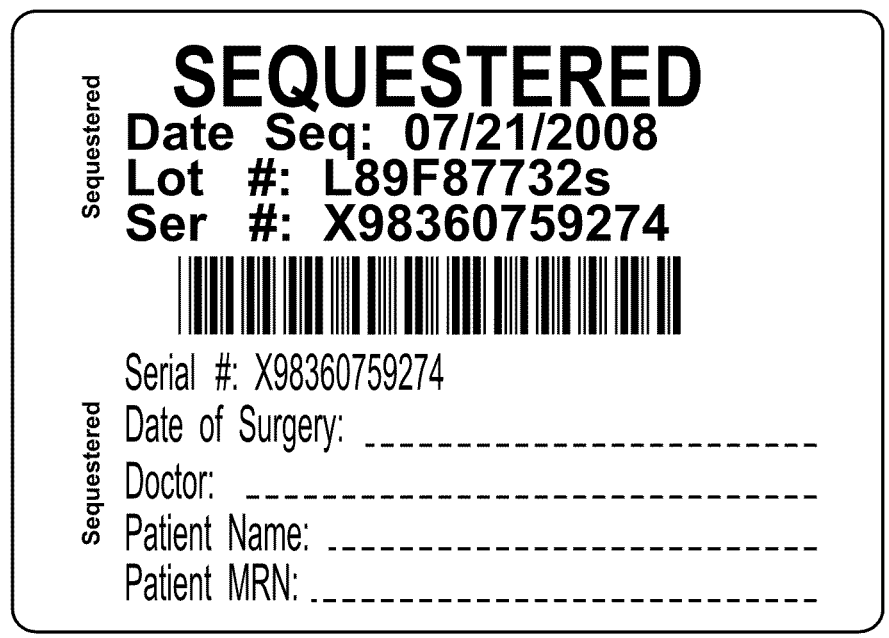
FIG. 10 shows an example of a label that can be printed and affixed to a sequestered tissue according to some embodiments.

In some embodiments, when the temperature within storage cabinet 130 is found to be out of range, the tissue stored within the storage cabinet 130 can be sequestered. In some embodiments, tissue can be sequestered based on a request from the tissue source facility based, for example, on information from the source regarding infection or disease of the source. In some embodiments, tissue can be sequestered based on an internal investigation. In some embodiments, tissue can be sequestered based on an adverse event that may be indicated by an external notification or an internal detection. An adverse event may include tissue born infection, tissue disease, bacterial infection, etc. Whatever the reason of the sequestration, tissue can be flagged as sequestered within tissue data server 110. In some embodiments, sequestered tissue can be flagged based on the tissue serial number. When tissue is flagged as sequestered, a label may be printed using printer 131 at a storage cabinet or with printer 151 at a user station. The label can include the word SEQUESTERED boldly printed so that it is easily noticeable as shown in FIG. 10. The label may contain the serial number of the tissue and other information germane to the sequestering of the tissue.

Figure 9:
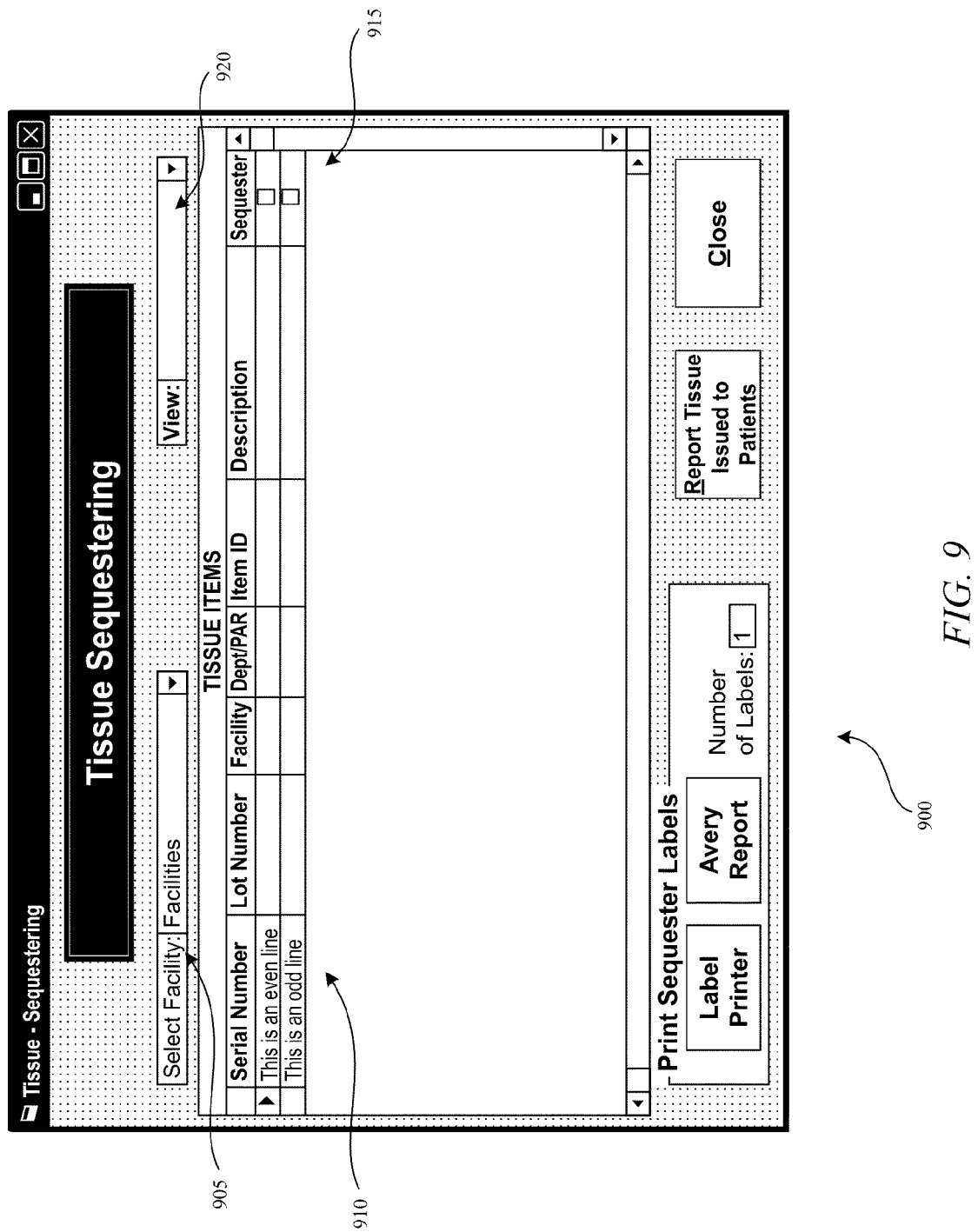
FIG. 9 shows an example of screenshot that can be used to manage sequestered tissue according to some embodiments.
Figure 11A:
FIG. 11A and FIG. 11B show examples screenshot alerting a user that requested tissue is sequestered according to some embodiments.
Figure 11B:

In some embodiments, when an attempt is made to restock, destock or issue sequestered tissue to a patient, a warning message can be displayed to the user as shown in FIG. 11A and/or FIG. 11B. In some embodiments, a user may be required to acknowledge the warning message before they are allowed to proceed and/or an indication that the user made such an acknowledgement can be stored in tissue data server. The user may be required to acknowledge the warning before the warning may be cleared. An acknowledgement that the warning was read can be stored at tissue data server 110 along with, for example, a time stamp, a user ID, a storage cabinet ID, etc. If an attempt is being made to issue the tissue to a patient, the tissue may not be issued and in some embodiments, the cabinet can remain locked so that the tissue cannot be issued to a patient. Sequestered tissue that has been determined to be safe for implant to a patient can also be freed for issuance from a Tissue Tracking module (e.g., as shown in FIG. 9) using user terminal 150 or storage cabinet 130.

When tissue is sequestered a sequestered label may automatically print, using printer 131 and the label can be attached to the sequestered tissue. The number of labels printed may be determined by the value of the Number of Labels in the system and/or the number of samples of tissue. A user may be able to print Sequestered labels at anytime by selecting an item or items in the grid and clicking the Print Sequester Label button.

In some embodiments, tissue may be issued to a patient, user, floor, department, etc., from storage cabinet 130. In some embodiments, tissue can be issued from patient specific bin 133. In some embodiments, prior to issuing tissue, any or all of the following information may be required from a user and/or communicated to tissue data server 110: tissue type, serial number, expiration date, issue date and/or time, user identifier, a response from the user whether the tissue integrity is acceptable, a response from the user whether the storage conditions were acceptable, patient information, patient medical record number, etc. Such information can be communicated from storage cabinet 130 to tissue data server 110 and stored in association with the tissue serial number. Moreover, in some embodiments, some information can be received from a user after issuance.

Figure 12:
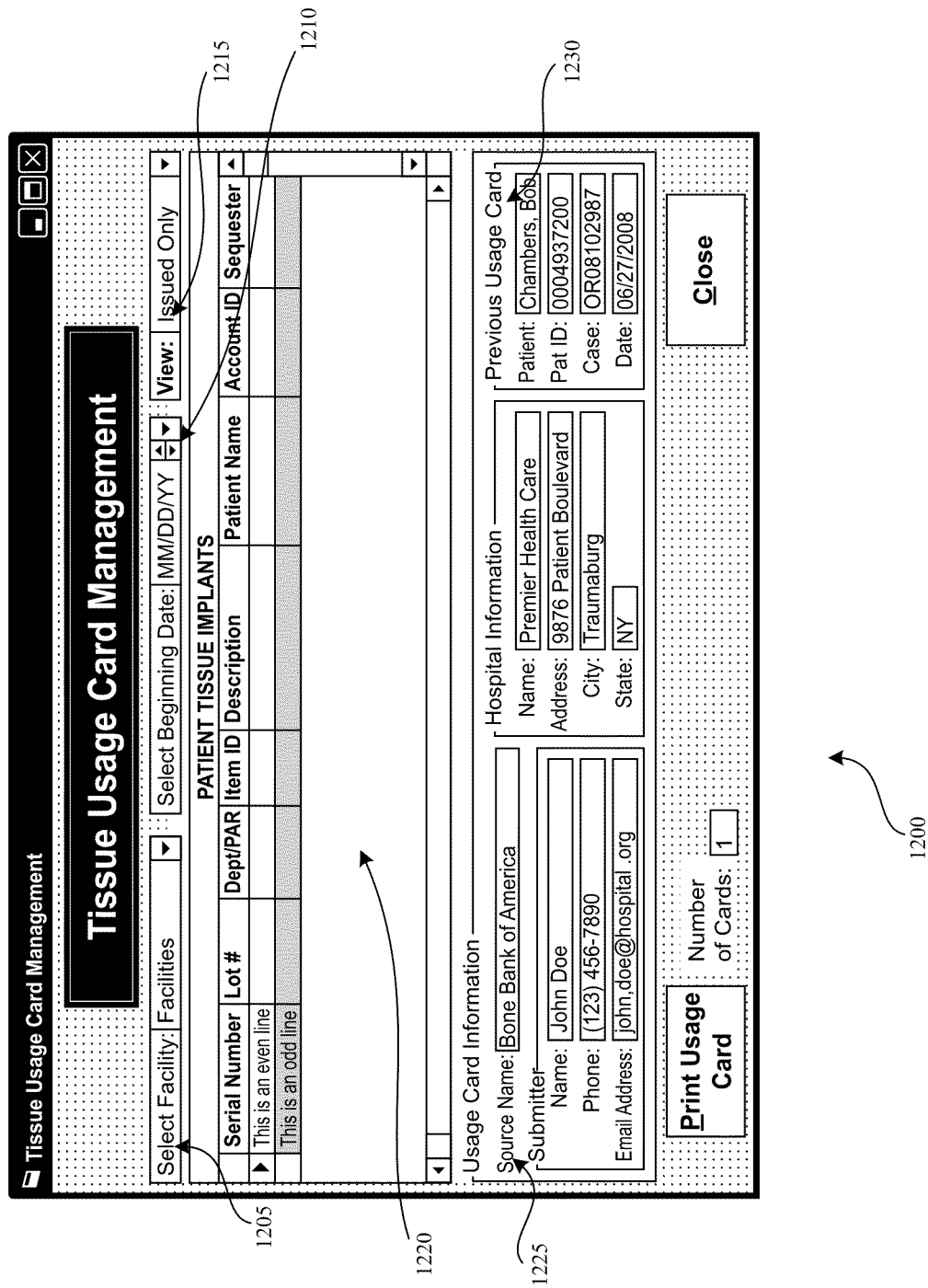
FIG. 12 shows an example of a screenshot of a tissue usage card manager according to some embodiments.

In some embodiments, if the tissue is autograft tissue, further information can be required at issue or at a later time from a user, either at storage cabinet 130 and/or at user terminal 150. In some embodiments, two unique identifiers can be required identifying the donor and/or the recipient. The identifiers, for example, can include donor and/or recipient name and/or donor and/or recipient record number. In some embodiments, if the tissue is autograft tissue, the user can be prompted to confirm that the donor and recipient are the same. In some embodiments, if the patient and donor information are not the same, an alert (e.g., as shown in FIG. 12) can be displayed to the user.

In some embodiments, tissue may be restocked into a storage cabinet 130 after it has previously been issued. In some embodiments, when tissue is restocked a unique tissue serial number can be created, stored in tissue storage server 110, and linked with the previous serial number. In some embodiments, the tissue's previous serial number can be used. A bar code with the new serial number can be printed using printer 131 and/or an RFID tag can be encrypted with RFID encode device 135. The patient's name and/or medical record number can also be entered. In some embodiments, the tissue type, a description, expiration date, restock date, and user identification can also be entered. Tissue integrity with or without comments can be received from a user as well as information detailing storage conditions with or without comments.

In some embodiments, a storage cabinet 130 can send an indication to tissue data server 110 and/or ordering subsystem 125 indicating that supply of a tissue within the storage cabinet has dropped below a threshold, an indication that tissue is being stocked within storage cabinet 130, and/or that tissue is being issued from storage cabinet 130. In some embodiments, tissue data server 110 can monitor tissue supply in each storage cabinet 130 and make a request when tissue supply has dropped below a threshold. In some embodiments, storage cabinet 130 can include a computer system that maintains a record of tissue stored within the storage cabinet 130, can monitor the tissue supply within storage cabinet 130, and/or storage cabinet 130 can make a request for new tissue when supply has dropped below a threshold. In some embodiments, storage cabinet 130 can also issue and/or receive tissue, monitor and store environmental factors, update tissue records, and/or perform other functions described herein in relation to tissue data server 110.

In some embodiments, a storage cabinet 130 can include an onboard computer (e.g., processor, user terminal, etc.). In some embodiments, any of the various tasks, processes, methods, data management, etc. that are described in association with a data server can also be performed at the onboard computer. For example, supply management can occur at the storage cabinet's onboard computer. As another example, data records can also be stored at the storage cabinet's onboard computer.

In some embodiments, only licensed users can access tissue within storage cabinet 130. A user, for example, can be required to provide a user identifier prior to stocking, restocking, destocking, and/or issuing tissue. If the user id is not associated with a licensed user, the user will not be able to stock, destock, restock and/or issue tissue.

In some embodiments, storage cabinet 130 can include dispensing units that provide access control to latched storage locations, such as those described in whole or in part in U.S. Pat. Nos. 5,805,455, 6,609,047, or 6,272,394, each titled "Methods and apparatus for dispensing items," the disclosures of which is herein incorporated by reference for all purposes. In some embodiments, storage cabinet 130 can include configurable dispensing units including touch-activated items, such as those described in whole or in part in U.S. Pat. Nos. 6,385,505 or 6,760,643, both titled "Methods and apparatus for dispensing items," the disclosures of which is herein incorporated by reference for all purposes.

In some embodiments, storage cabinet 130 can include dispensing units and/or methods for dispensing products, such as those described in whole or in part in U.S. Pat. No. 5,805,456, titled "Device and method for providing access to items to be dispensed," the disclosure of which is herein incorporated by reference for all purposes.

In some embodiments, dispensing units that provide lockable units, such as those described in whole or in part in U.S. Pat. Nos. 5,905,653 or 5,745,366, each titled "Pharmaceutical dispensing device and methods," the disclosures of which is herein incorporated by reference for all purposes. In some embodiments, dispensing units can include drawers and/or lids with or without locks, such as those described in whole or in part in U.S. Pat. Nos. 5,927,540, 6,011,999, 6,170,929, or 5,377,864 the disclosures of which is herein incorporated by reference for all purposes.

In some embodiments, storage cabinet can include light guiding bins and/or cabinets, such as those described in whole or in part in U.S. Pat. No. 6,039,467, titled "Lighting system and methods for a dispensing device," the disclosure of which is herein incorporated by reference for all purposes.

In some embodiments, storage location 130 can include restocking methods and/or liners, such as those described in whole or in part in U.S. Pat. No. 6,640,159, titled "Replacement liner and methods for a dispensing device," the disclosure of which is herein incorporated by reference for all purposes.

In some embodiments, storage location 130 can include devices and/or methods, such as those described in whole or in part in U.S. Pat. No. 6,151,536, titled "Dispensing system and methods," the disclosure of which is herein incorporated by reference for all purposes.

In some embodiments, tissue tracking system 100 can methods for consolidating purchase orders and/or for supplying items, such as those described in whole or in part in U.S. Pat. No. 7,072,855, titled "Systems and methods for purchasing, invoicing and distributing items," the disclosure of which is herein incorporated by reference for all purposes.

In some embodiments, tissue tracking system 100 can include devices and/or methods, such as those described in whole or in part in U.S. Pat. No. 5,190,185, titled "Medication transport and dispensing magazine," the disclosure of which is herein incorporated by reference for all purposes.

In some embodiments, tissue tracking system 100, such as those described in whole or in part in U.S. Pat. No. 6,975,922, titled "Secured dispensing cabinet and methods," the disclosure of which is herein incorporated by reference for all purposes.

In some embodiments, tissue tracking system 100 can track tissue using RFID cabinets, labels, readers and so forth, such as those described in whole or in part in U.S. Pat. Nos. 7,218,231 or 7,348,884 the disclosures of which is herein incorporated by reference for all purposes.

In some embodiments, tissue tracking system 100 can include a portable medication cart, such as those described in whole or in part in U.S. Pat. No. 6,604,019, titled "Automated pharmaceutical management and dispensing system," the disclosure of which is herein incorporated by reference for all purposes.

In some embodiments, tissue tracking system 100 can also include a billing subsystem 120. In some embodiments, billing subsystem 120 can be a standalone billing subsystem. In some embodiments, billing subsystem 120 can be any type of billing system for managing and paying purchase orders. When tissue is received a purchase order number can be entered indicating that at least the portion of the purchase order relating to the tissue has been fulfilled. Once a purchase order has been fulfilled, the billing system can implement payment for the tissue.

In some embodiments, tissue tracking system 100 can also include an ordering subsystem 125. In some embodiments, ordering subsystem 125 can be implemented as part of tissue data server 110. In some embodiments, ordering subsystem 125 can track the stock and/or location of tissue by type. In some embodiments, ordering subsystem 125 can order tissue from suppliers when tissue in stock drops below a threshold level. For example, ordering subsystem 125 can create purchase orders and initiate and/or carryout the automated ordering of tissue from suppliers. In some embodiments, ordering subsystem 125 can manage tissue stock levels within a plurality of storage cabinets 130. For example, ordering subsystem 125 can monitor whether tissue within one of the plurality of cabinets 130 is below a threshold level. If tissue supply within a storage cabinet drops below the threshold, the ordering subsystem 125 can direct transfer of tissue from one storage cabinet to another in order to maintain supply within each cabinet at levels above threshold.

In some embodiments, tissue ordering and management functions can be maintained using ordering subsystem 125. In some embodiments, tissue can be automatically ordered from a source facility to replenish depleted inventory.

In some embodiments, tissue tracking system 100 can include a patient file server 112 that contains patient files. In some embodiments, patient file server 112 can be a standalone subsystem and/or a separate subsystem that is networked with tissue tracking system 100. Tissue tracking system 100, in some embodiments, can provide tissue information to patient file server 112 for inclusion in a patient file. In some embodiments, patient information from patient file server 112 can be communicated to tissue data server 110 for inclusion in tissue records.

Figure 2:
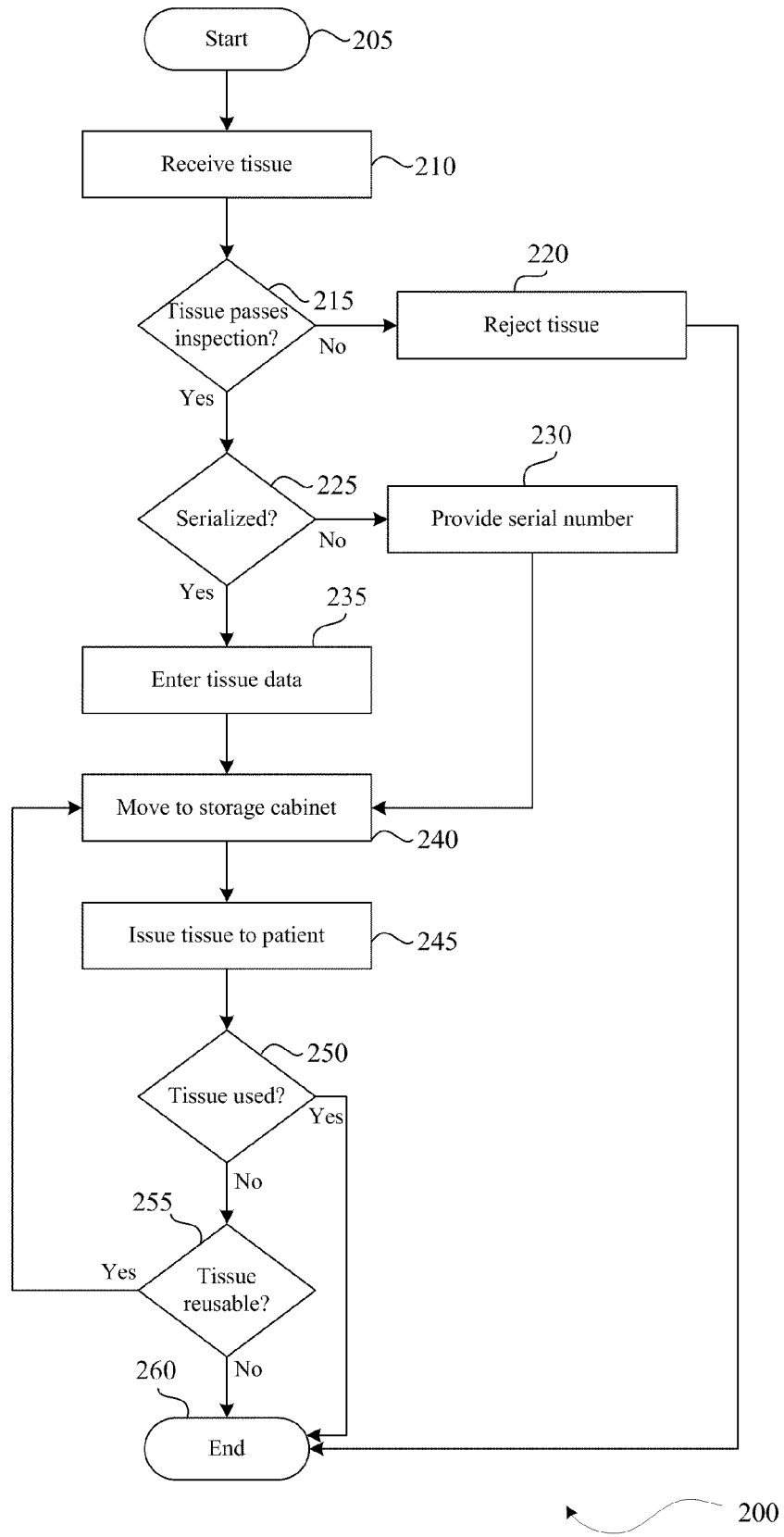
FIG. 2 is a flowchart of a processes for receiving tissue from a supplier according to some embodiments.

FIG. 2 is a flowchart of a process 200 of tissue moving from reception to issuance according to one embodiment. Process 200 starts at block 205; at block 210 tissue is physically received at a facility. Tissue can be received from a source using any type of delivery. In some embodiments, delivery can be required to maintain specific environmental factors at set levels. For example, some tissue may be required to be stored and transported at a set temperature. Hence, in such examples, delivery can occur that maintains a set temperature. At block 215 a user can determine if the tissue passes inspection that can include whether the tissue was transported within environmental requirements and/or whether the tissue packaging is undamaged. For example, a temperature report can be viewed to make the determination. If the inspection fails, tissue is rejected at block 220 and process 200 ends at block 260.

If the tissue passes inspection at block 215, a user can determine if the tissue was previously serialized at block 225. In some embodiments, blocks 215 and 225 can be interchanged in their order. In some embodiments, tissue from some vendors can arrive serialized. Tissue from other vendors can arrive unserialized or use a serial number that is unacceptable. If the tissue requires serialization, a serial number can be provided by tissue tracking system at block 230. In some embodiments, the serial number can be encoded into a barcode and printed onto a label. In some embodiments, the serial number can be encoded into an RFID tag, associated with an RFID tag value, and/or printed onto a label. The label with the serial number can then be affixed to the tissue. In some embodiments, a label with a barcode representing the serial number of serialized tissue can also be printed and affixed to tissue. In some embodiments, an electronic file can be received and/or downloaded from a vendor that includes serialization information and/or source information.

Tissue data can be entered into the system at block 235. Tissue data can include tissue integrity information, packaging integrity information, temperature levels during transport, source facility, billing entity, billing address, amount of bill, purchase order number, user identification, receiving department, time and data of reception, expiration date, department, tissue type, etc. Such information can be entered using a user terminal (e.g., user terminal 150 shown in FIG. 1).

The tissue can then be stored in a storage cabinet at block 240. For example, the tissue can be stored in storage cabinet 130 shown in FIG. 1. In some embodiments, tissue can be placed within patient specific storage bin 133 at storage cabinet 130. Tissue can be issued from a storage cabinet to a patient at block 245. At issuance, a user can enter various information such as tissue type, serial number, expiration date, issue date and/or time, user identifier, a response from the user whether the tissue integrity is acceptable, a response from the user whether the storage conditions were acceptable, patient information, patient medical record number, etc. Various other information can be requested by the system. An example of a screenshot of an interactive display for issuing tissue is shown in FIG. 3.

Tissue that was issued at block 245 can go unused and can be reentered into inventory. Hence, at block 250 process 200 determines whether the tissue was used and at block 255 whether the tissue is reusable. If the answer to block 250 is no and 255 is yes, then the tissue is placed back into storage at block 240. If the answer to block 250 is yes or block 255 is no, then the process ends at block 260.

Figure 3:
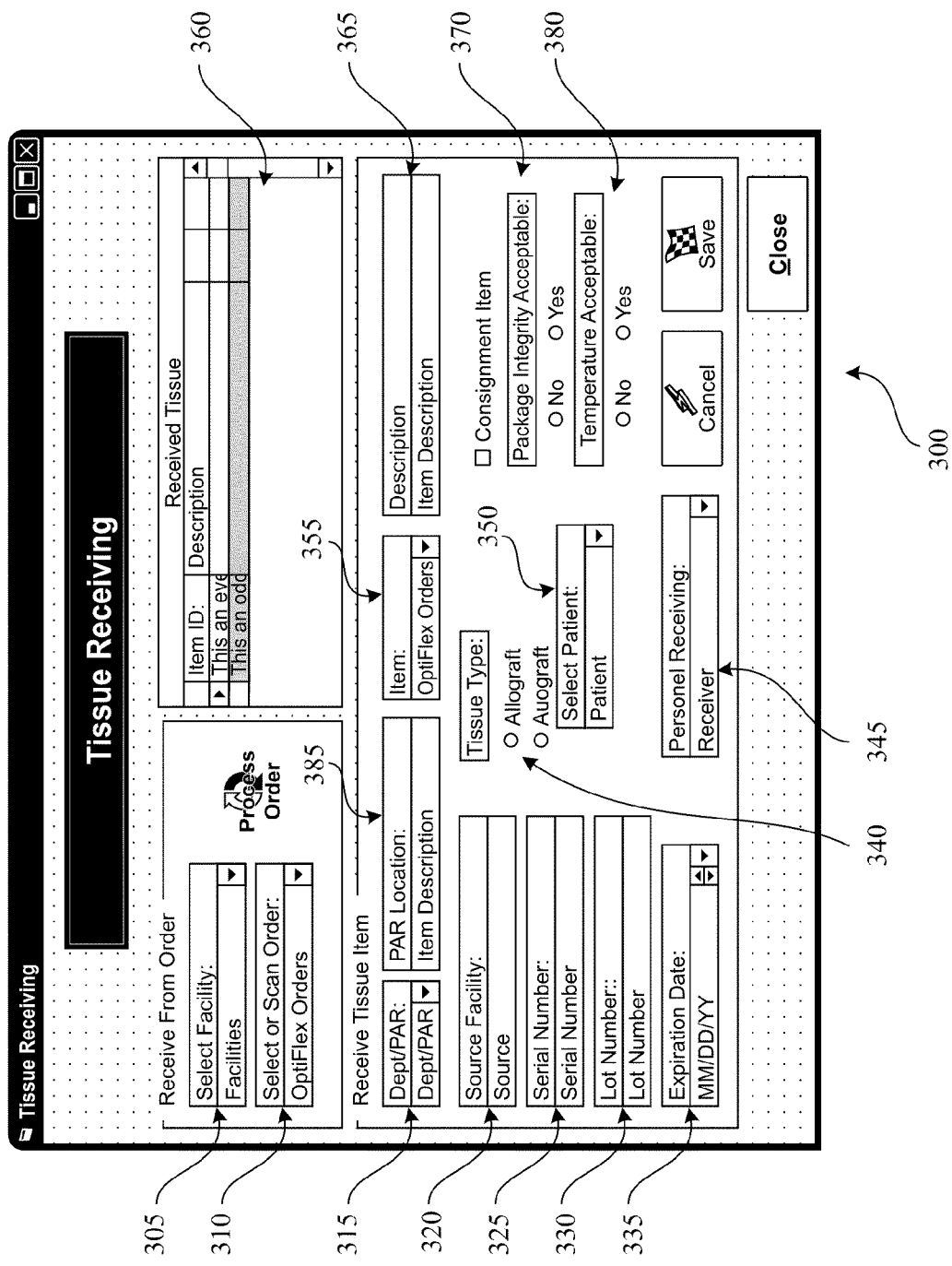
FIG. 3 shows an example of a screenshot that can be used to receive tissue.

FIG. 3 shows an example of screenshot 300 that can be used to receive tissue. In some embodiments, screenshot 300 provides a user with data entry fields that can be used to collect data for one or more tissues when they are received at a station. In some embodiments, various other data entry fields can be used and/or some deleted. Moreover, some data entries can be pre-populated based on scanning a barcode and/or from the purchase order.

In some embodiments, data entry fields can include facility field 305 that can be used to enter the facility receiving the tissue. In some embodiments, order entry field 310 can be used to select an order from within a supply chain management system. In some embodiments, a purchase order can be scanned and order entry field 310 can be automatically populated. In some embodiments, a user can enter a department where the tissue is being received in department entry box 315. The source facility of the tissue can be entered in source facility entry box 320. Serial and lot numbers can be entered in serial number entry box 325 and lot number entry box 330 respectively.

The expiration date of the tissue can be entered in expiration entry box 335. Tissue type can be entered using radio buttons 340. In this example, the tissue type can be entered as either an allograft or autograft tissue. If the tissue is autograft tissue, the patient associated with the autograft tissue can be selected using drop down menu 350. In some embodiments, the patient name and/or patient number can be entered using a text entry box. The name and or user id of the receiving individual can be entered in receiver drop down menu 345. The item within a purchase order can be selected using drop down menu 355. Box 360 can display tissue information for tissue received as part of the purchase order entered or automatically populated in box 310.

Item description box 365, in some embodiments, can be used to enter and/or display the item description. For example, the description can be pulled from the purchase order and/or entered by the receiving user. Block 370 can be used by a user to input whether the package integrity is acceptable. Block 380 can be used by a user to input whether the temperature under which the tissue was transported and/or received is acceptable. Block 385 can be used to enter the par location of the tissue.

Some information provided in screenshot 300 can be auto populated based, for example, on a scanned bar code and/or based on selecting the tissue within the received tissue field 360. In some embodiments, information in screenshot 300 can be entered by a user at a user terminal 150.

In some embodiments, prior to entering receiving information as shown in FIG. 3, a user can be prompted for a serial number. The serial number can be scanned and/or manually entered as shown in screenshot 400 of FIG. 4. For example, the serial number can be scanned using bar code scanner 133 or 153 and/or RFID scanner 134 or 154. Moreover, various other tasks, such as moving tissue from one location to another, destocking tissue, restocking tissue, issuing tissue, etc. can require entry of a serial number in block 405 prior to further data entry and/or accessing the tissue. In some embodiments, once the serial number has been entered, data can be retrieved (e.g., for example, from tissue server 110) and/or data can auto populate into other data entry fields in various other screenshots.

FIG. 5 shows screenshot 500 of form for entering data prior to issuing tissue from a storage cabinet (e.g., storage cabinet 130 of FIG. 1) according to some embodiments. In some embodiments, less or more information can be collected prior to issuance. In this embodiment, the user is prompted to enter or scan the serial number of the tissue at block 505. For example, the serial number can be scanned using bar code scanner 133 or 153 and/or RFID scanner 134 or 154. Information about the user preparing the tissue is entered at block 510. The information about the user preparing the tissue can include, for example, user id, user name and/or date and time of preparation. Information about the user accepting the tissue is entered at block 515. The information about the user accepting the tissue can include, for example, user id, user name and/or date and time of preparation. Information about the user issuing the tissue is entered at block 520. The information about the user issuing the tissue can include, for example, user id, user name and/or date and time of preparation. In some embodiments, a user can simply enter a user id and their user name can be auto populated. In some embodiments, a user can enter only the user name.

Information can be entered by the user prior to issuing the tissue using a touch screen, a keyboard, a barcode scanner, a bio-scanner, RFID scanner, etc. In some embodiments, the shelf where the tissue stored can be scanned and/or displayed on screenshot 500. The shelf number, in some embodiments, can be required to match the shelf number of the tissue. In some embodiments, the tissue type can also be displayed on screenshot 500.

In some embodiments, the user preparing the tissue and the user accepting the tissue cannot be the same user as the user issuing the tissue.

Figure 6:
FIG. 6 shows an example of a screenshot warning a user that autograft tissue is from a patient different than the patient for whom the tissue is being requested according to some embodiments.
Figure 6:
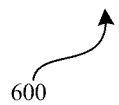

In some embodiments, when an autograft tissue is being issued, a check will be made to ensure that the tissue being issued was taken from the same patient to whom the tissue is being issued. In some embodiments, the check can be made after the serial number of the tissue item has been entered and the patient from which the tissue was taken can be identified. In some embodiments, patient medical numbers can be matched with a medical record number associated with the autograft tissue. In some embodiments, if there is a match between the patient and the patient from whom the tissue was harvested, the tissue can be issued. If, however, there is not a match between the patient and the patient from whom the tissue was harvested a warning message as shown in screenshot 600 of FIG. 6 that can be displayed indicating that the tissue is autograft and cannot be issued to a patient other than the patient from which the tissue was harvested. In some embodiments, an indication that the user acknowledge the warning shown in FIG. 6 can be stored in association with the tissue records.

In some embodiments, tissue tracking system 100 can include components provided by Omnicell, Inc. of Mountain View, Calif. For example, an OptiFlex Surgical Services system and/or OmniSupplier system can be used as a tissue storage cabinet 130.

Figure 7:
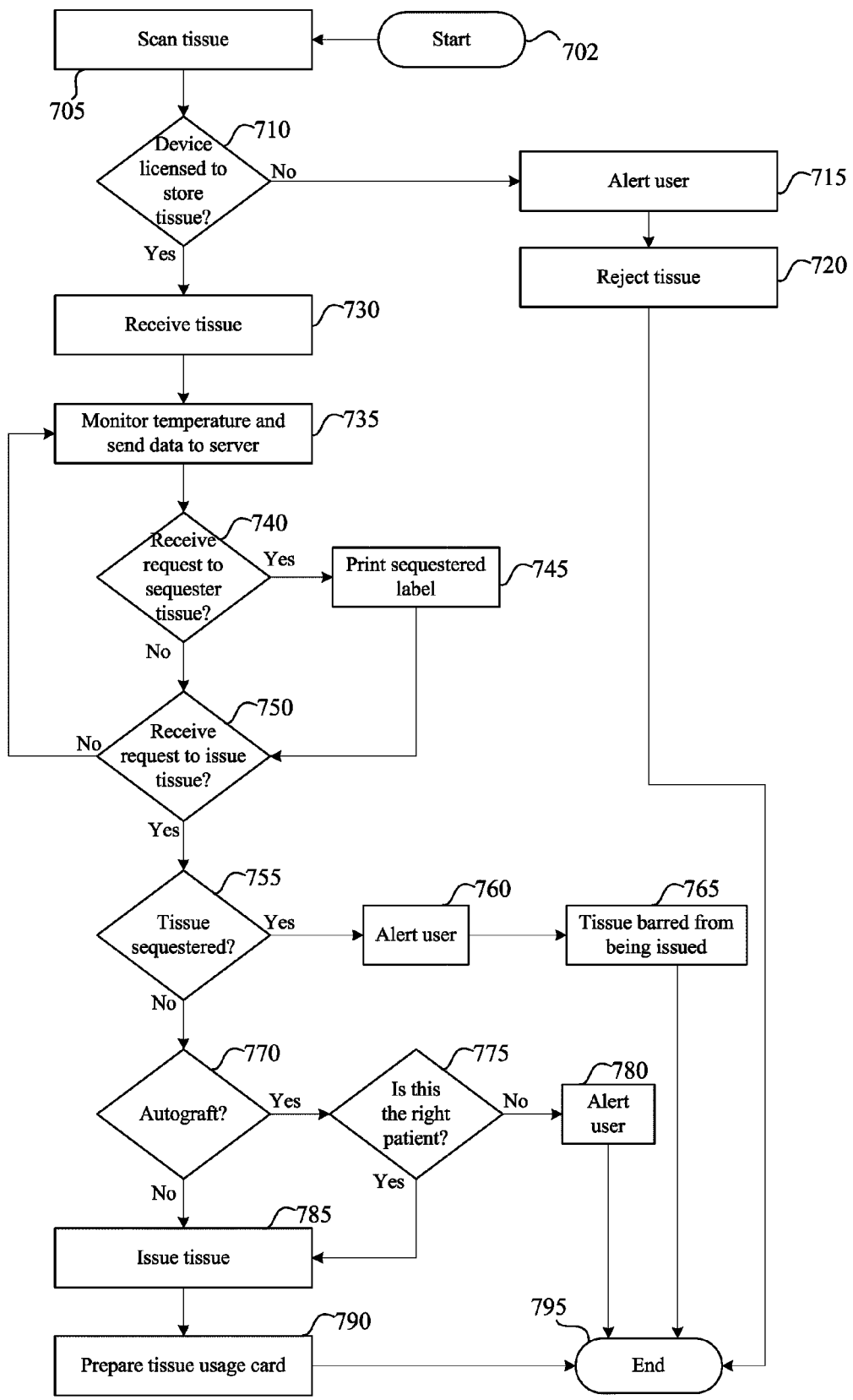
FIG. 7 is a flowchart of process for issuing tissue from a storage cabinet according to some embodiments.
Figure 8:
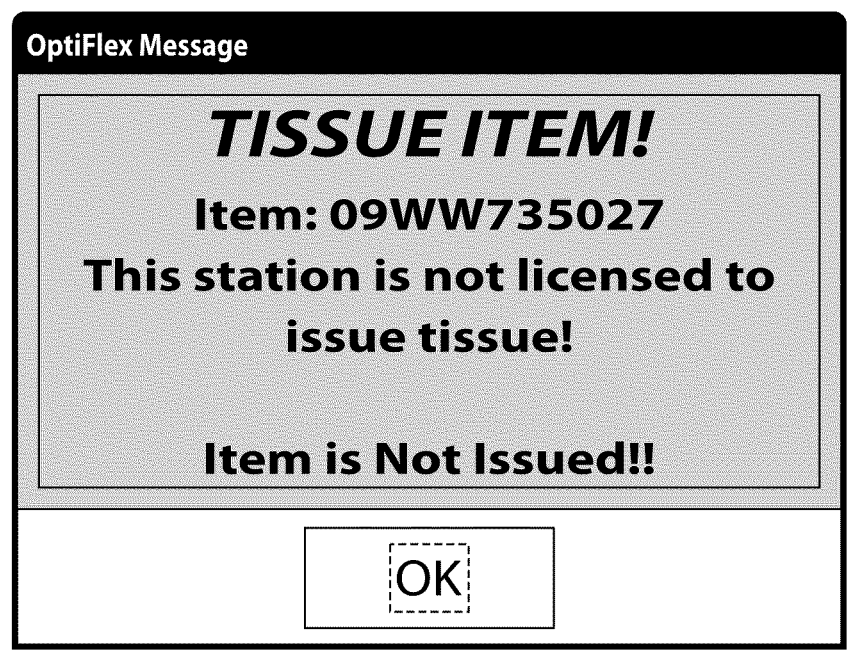
FIG. 8 shows an example of a screenshot warning a user that a storage cabinet is not licensed for tissue storage according to some embodiments.

FIG. 7 shows a flowchart of process 700 for receiving tissue at a storage cabinet and issuing tissue to a user according to some embodiments. Process 700 starts at block 702. At block 705 a user can scan the barcode of tissue that they wish to store in a storage facility, for example, using bar code scanner 133 or 153 and/or RFID scanner 134 or 154. In some embodiments, rather than scan the barcode, the user can enter the serial number of the tissue (e.g., entering data as shown in screen shot 400 of FIG. 4). At block 710, process 700 can determine whether the storage cabinet is licensed to store tissue. If the storage cabinet is not licensed for tissue storage, in some embodiments, an alert can be displayed to the user at block 715, for example, at a user terminal display, and the tissue is rejected for storage in storage facility at block 720. Process 700 can then end at block 795. FIG. 8 shows screenshot 800 that is an example of an alert displayed to a user when the user attempts to storage tissue in an unlicensed storage cabinet.

Returning to FIG. 7, if the storage facility is licensed to store tissue at block 710 the tissue can be received at block 730. An indication, for example, that the tissue is stored in the storage facility can be sent and stored to a central server (e.g., tissue data server 110 of FIG. 1). The indication can, for example, include the tissue serial number, the date, the time, the user placing the tissue in storage, etc.

In some embodiments, the temperature within the storage cabinet can be monitored at preset frequencies and the temperature data sent to a central server at block 735. In some embodiments, temperature data can be recorded periodically at a predetermined frequency. In some embodiments, a user can enter the frequency of temperature measurements. In some embodiments, a minimum threshold temperature and/or maximum threshold temperature can be entered or a default maximum threshold temperature and/or minimum threshold temperature can be used to determine if the temperature falls without acceptable ranges. In some embodiments, if the measured temperature goes above the maximum threshold temperature or below the minimum threshold temperature, an audible and/or visual alarm may sound, a temperature reading may be logged, and/or an email, page, voicemail, text message, etc. can be sent to a previously indicated person. In some embodiments, when the temperature is found to be out of range, a "Temperature Out of Range" report may be created that indicates the storage cabinet, date, time, cabinet temperature, and/or allow for system administrator to document temperature alarm resolution.

In some embodiments, a temperature at issuance report may be generated. This report may provide temperature data at time of issue, by patient, and/or by date. The report may also provide the ability to query the system by patient for temperature at time of issue. The report may also include selection criteria based, for example, on patient, serial number and/or date. Such a report may include filed for: item, Description, Serial Number, Patient/Location, Transaction Date, Temperature, Usage. Such a report may allow for sorting by item, Description, Serial Number, Patient/Location, and/or Transaction Date.

In some embodiments, tissue within a storage facility can automatically be flagged as sequestered when the temperature measurements lie without acceptable ranges. In some embodiments, tissue records stored in a central server can indicate if the tissue is flagged as sequestered. If the tissue is flagged as sequestered at block 740, then a sequestered label can be printed at block 745. FIG. 10 shows an example of a tissue sequestration label that can be printed in block 745. Tissue sequestering can occur when temperature falls outside of acceptable ranges, when the expiration data of the tissue has expired, and/or when an indication is received from a source facility that tissue should be sequestered.

Tissue stored within a storage facility can be ready for issuance from storage. In some embodiments, if the tissue is not being issued as determined in block 750 the tissue remains in storage and the temperature will continue to be monitored in block 735. If the a request to issue tissue is received at block 750 (e.g., using tissue issue entry as shown in FIG. 5), the system can determine whether the tissue has been flagged as sequestered at block 755. If the tissue is flagged as sequestered, the user can be alerted at block 760 (e.g., using an alert similar to the one shown in FIG. 11A and/or FIG. 11B). If the tissue is flagged as sequestered the tissue is barred from being issued at block 765 and process 700 ends at block 795. In some embodiments, data entry fields may not allow entry when a sequestered tissue is selected for issuance. In some embodiments, locks on the storage cabinet may not open when a tissue flagged as sequestered is selected for issuance. In some embodiments, the sequestered flag can be removed by a system administrator or another user.

If the tissue is not flagged as sequestered at block 755, then block 770 determines whether the tissue is an autograft tissue. If the tissue is autograft tissue, then system records will so indicate. The system can lookup the records to determine whether the tissue is autograft tissue. If the tissue is autograft tissue, at block 775 it is determined whether the patient from which the tissue was harvested is the same as the patient to whom the tissue is being issued. A comparison of medical record numbers associated with the autograft tissue and/or the patient can be used to make this determination. If there is not a match, the user is alerted at block 780 (e.g., as shown in screenshot 600 of FIG. 6), and process 700 can end. In some embodiments, the user can be queried to select a different tissue and/or patient. If the tissue is not autograft tissue at block 770 or if the tissue is autograft and there is a match with the patient at block 775, then the tissue is issued at block 785. Following issuance, a tissue usage card can be prepared and printed (e.g., see FIG. 12 and FIG. 13). In some embodiments, a user may be required to enter information for the tissue usage card at block 790. Process 700 ends at block 795.

FIG. 8 shows an example of a screenshot 800 warning a user that a storage cabinet is not licensed for tissue storage according to some embodiments. In some embodiments, when a user requests autograft tissue for issuance, the storage cabinet can request that the user enter the patient record number. If the patient record number entered by the user does not match the patient record number of the patient from which the autograft was harvested, screenshot 800 can be used to warn the user that the tissue is not issued.

FIG. 9 shows an example of screenshot 900 that can be used to manage sequestered tissue according to some embodiments. As shown in screenshot 900, various fields can be used by a user to enter data, manipulate data, etc. In some embodiments, a user can be requested to select a facility in facility combo box 905. Doing so allows the user to view tissue flagged as sequestered at the selected facility. In some embodiments, the tissue serial number, lot number, facility, department, PAR, item id, and a tissue description can be displayed for each facility at block 910. In some embodiments, a sequestered check box 915 can also be used to allow a user to flag and/or un-flag tissue as being sequestered. In some embodiments, a user can use view combo box 920 to view all tissue items, sequestered tissue items, and/or unsequestered tissue items.

FIG. 10 shows an example of label 1000 that can be printed and affixed to a sequestered tissue according to some embodiments. Label 1000 can be printed at a user terminal 150, storage cabinet 130 or any other location. Label 1000 can include the term "SEQUESTERED" in large type face and/or in different colors, such as red. The label, in some embodiments, can also include the data the tissue was sequestered, the tissue lot, the tissue serial number, a bar code, a label serial number, a surgery date, a doctor name and/or id number, a patient name and/or patient serial number.

Figure 13:
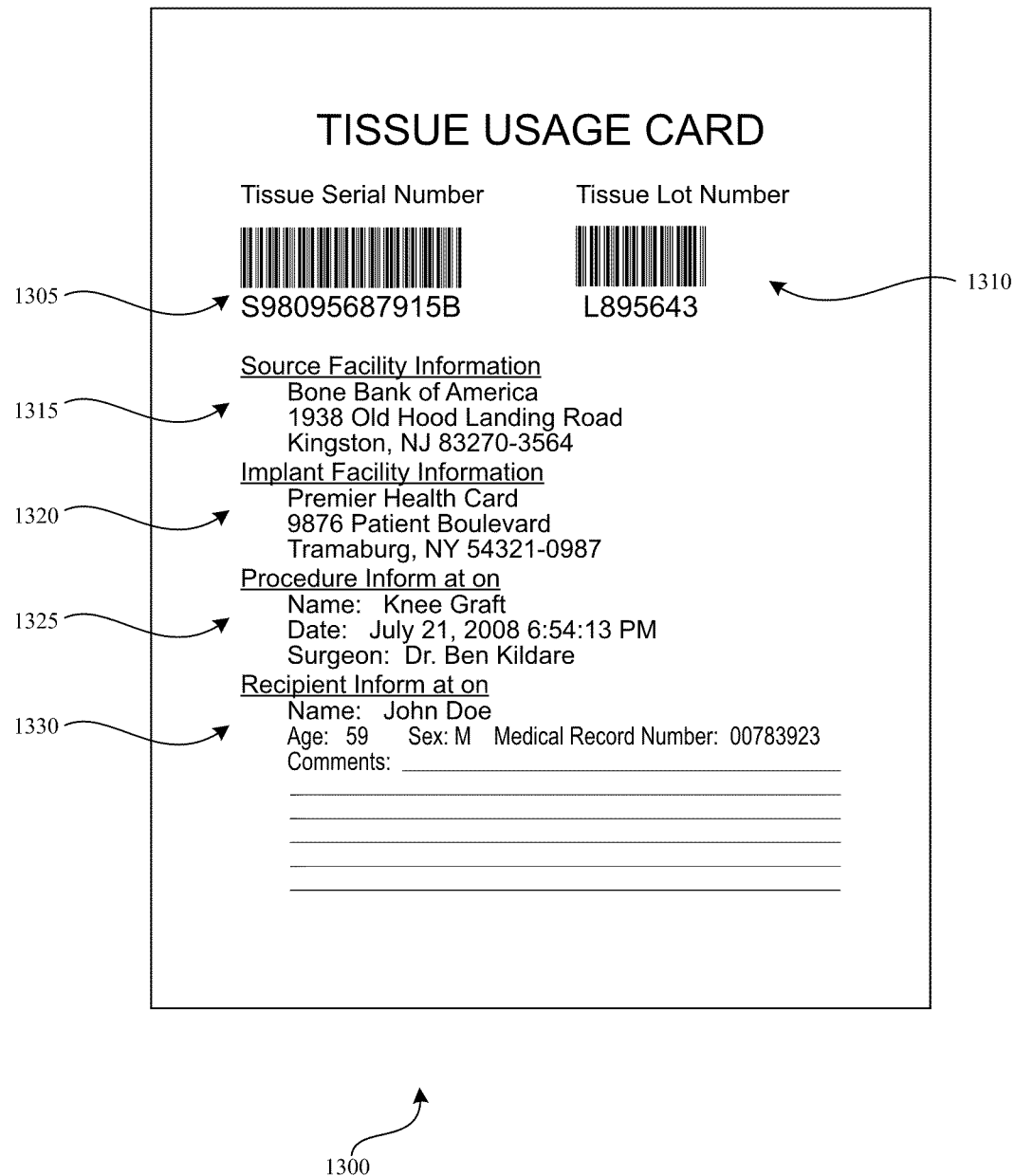
FIG. 13 shows an example of a tissue usage card according to some embodiments.

FIG. 12 shows an example of a screenshot 1200 of a tissue usage card manager according to some embodiments. An example of a tissue usage card 1300 is shown in FIG. 13. A tissue usage card can be returned to the source facility with the patient issue information. In some embodiments, a tissue usage card can be sent to the source facility as an email, letter, fax, document, electronically, or any other data transfer mechanism. Screenshot 1200 shows a form that can be used to select a tissue for which a tissue usage card is to be created. A tissue usage card can be created at a user terminal, at a storage cabinet, and/or any other location.

In some embodiments, a tissue usage card can be created specifying more than one tissue and/or more than one patients. In some embodiments, tissue usage cards can specify tissue used within a set or variable period of time using the data combo box 1210. In some embodiments, the options for display at screenshot 1200 can be selected in combo box 1215, for example to Issued Only, Unissued Only, or All Tissue Items. In some embodiments, the user can modify the facilities queried using the combo box 1205.

When a tissue item is selected from the patient tissue implants grid 1220, information that will be printed on the Usage Card is displayed in the area below the grid. The Source Name 1225 can be obtained from the information entered for the tissue when it was received. In some embodiments, if a usage card had been previously printed for the tissue, this information can be displayed in previous usage card box 1230. In some embodiments, this information may not be editable.

FIG. 13 shows an example of tissue usage card 1300 according to some embodiments. In some embodiments, tissue usage card 1300 can include information such as tissue serial number 1305 in characters and/or in barcodes and/or tissue lot number 1310 in characters and/or lot number. Other information can include source facility information 1315, implant facility information 1320, procedure information 1325, and/or recipient information 1330 including comments.

In some embodiments, documents for supplier FDA registration and/or state licensure can be automatically generated in a manner similar to issuing a tissue usage card. Some or all the data may be included. Additional data may be required.

What is claimed is:

1. A tissue tracking system comprising:
 a database for storing information associated with a sample of tissue;
 a computer system coupled with the database, the computer system being configured to associate a serial number with the tissue and to generate and store a record of issuance in the database indicating that the sample of tissue has been issued to a user, the record of issuance including the associated serial number and user identification information, wherein the computer system is configured to receive an indication that the tissue has been sequestered, wherein a tissue is sequestered based on notification indicating an adverse event related to the tissue, wherein the adverse event is selected from the group consisting of tissue born infection, tissue disease, bacterial infection, and the temperature of the tissue going of a range, and wherein the computer system includes instructions to record an indication in the database that the tissue has been sequestered;
 a user interface configured to receive a request from a user to issue the tissue; and
 a storage location configured to store the tissue, wherein the storage location includes a locking device that remains locked in response to the request from the user to issue the tissue when the tissue is flagged in the database as being sequestered, and wherein the locking device is unlocked when the tissue is requested for use with a patient and the tissue is not flagged in the database as being sequestered.

2. The tissue tracking system according to claim 1, wherein the computer system includes a device configured to receive the serial number from a user, wherein the device is selected from the group consisting of a barcode scanner, an RFID receiver, and a keyboard.

3. The tissue tracking system according to claim 1, wherein the computer system is configured to create the serial number that is associated with the tissue.

4. The tissue tracking system according to claim 1, wherein the computer system is coupled with a user interface at the storage location.

5. The tissue tracking system according to claim 1, wherein the storage location is configured to communicate time data to the database.

6. The tissue tracking system according to claim 1, wherein the storage location further comprises a processor configured to communicate a storage location identifier to the database.

7. The tissue tracking system according to claim 1, wherein the storage location includes a thermometer configured to measure a temperature within the storage location and wherein the temperature is communicated to the database at predetermined intervals.

8. The tissue tracking system according to claim 7, wherein the storage location further comprises a user interface configured to alert a user through the user interface when the recorded temperature exceeds a threshold temperature.

9. The tissue tracking system according to claim 1 further comprising a user interface configured to receive a patient identifier from a user, wherein the patient identifier is communicated to the database and stored in the database in association with the tissue serial number.

10. The tissue tracking system according to claim 1 wherein the computer system is configured to receive a patient identifier, wherein the record of issuance is generated and stored in the database indicating that the sample of tissue has been issued when the received patient identifier matches a patient identifier associated with the tissue in the database.

11. The tissue tracking system according to claim 10, wherein the computer system is configured to alert the user when the patient identifiers do not match.

12. The tissue tracking system according to claim 1 further comprising means for producing a tissue usage card when the tissue has been issued to a patient.

13. The tissue tracking system according to claim 12, wherein the means for producing a tissue usage card comprises a printer.

14. The tissue tracking system according to claim 12, wherein the tissue usage card includes information comprising at least one of tissue source information, tissue source facility information, implant facility information, patient information, procedure information, procedure date, tissue serial number, and sequestration information.

15. The tissue tracking system according to claim 1 wherein the user interface is configured to alert the user when the tissue is flagged as being sequestered.

16. A method for issuing tissue from a tissue storage device that includes a lock, the method comprising:
receiving at a computer system having a database an indication that an adverse event related to a tissue sample has occurred, wherein the adverse event is selected from the group consisting of tissue born infection, tissue disease, bacterial infection, and the temperature of the tissue going out of a range;
flagging a record associated with the tissue sample in the database of the computer system in response to the indication that the tissue sample is sequestered;
thereafter receiving a request to issue the tissue sample from a user, wherein the request is received through a user interface communicatively coupled with the tissue storage device;
in response to receiving the user request, determining with the computer system that the record stored in the database and associated with the tissue sample indicates that the tissue has been flagged as sequestered; and
when the record associated with the tissue sample indicates that the tissue has been flagged as sequestered, not issuing the tissue by not unlocking the storage device and providing an indication in the record associated with the tissue sample that the tissue has not been issued in response to the user request.

17. The method according to claim 16 further comprising when the record associated with the tissue sample indicates that the tissue has been flagged as sequestered, alerting the user through a user interface that the tissue is sequestered.

18. A method for issuing tissue from a tissue storage device that includes a lock, the method comprising:
receiving at a computer system having a database a user request for a tissue sample stored in a storage device, wherein the user request is received through a user interface communicatively coupled with the tissue storage device, wherein the database includes a record associated with the tissue sample and the record includes a first patient identifier, wherein the tissue sample is selected from the group consisting of bone, cornea, skin, heart tissue, valve, conduit, tendon, ligament, fascia, dura, bone marrow, vein, artery, cartilage, organ tissue, sperm, embryo, muscle, egg, stem cell, cord blood, synthetic tissue, allograft tissue, autograft tissue, isograft tissue, and xenograft tissue;
receiving at the computer system through the user interface a second patient identifier from the user;
determining with the computer system whether the first patient identifier and the second patient identifier match;
when the first patient identifier and the second patient identifier match, unlocking the storage device, issuing the tissue, and providing an indication in the record associated with the tissues sample that the tissue has been issued; and
when the first patient identifier and the second patient identifier do not match, locking the storage device, and providing an indication in the record associated with the tissues sample that the tissue has not been issued.

19. The method according to claim 18 further comprising when the first patient identifier and the second patient identifier do not match, providing an indication in the record associated with the tissues sample that the tissue has not been issued.

20. The method according to claim 18 further comprising when the first patient identifier and the second patient identifier do not match, alerting the user through the user interface that the tissue is autograft tissue from a different patient.

* * * * *